United States Patent
Laugharn, Jr.

(10) Patent No.: US 9,335,237 B2
(45) Date of Patent: May 10, 2016

(54) SYSTEMS AND METHODS FOR ACOUSTICALLY PROCESSING TISSUES SAMPLES

(71) Applicant: Covaris, Inc., Woburn, MA (US)

(72) Inventor: James A. Laugharn, Jr., Winchester, MA (US)

(73) Assignee: Covaris, Inc., Woburn, MA (US)

( * ) Notice: Subject to any disclaimer, the term of this patent is extended or adjusted under 35 U.S.C. 154(b) by 69 days.

(21) Appl. No.: 13/911,197

(22) Filed: Jun. 6, 2013

(65) Prior Publication Data

US 2014/0363843 A1 Dec. 11, 2014

(51) Int. Cl.
*G01N 33/00* (2006.01)
*G01N 1/28* (2006.01)
*G01N 1/40* (2006.01)

(52) U.S. Cl.
CPC .............. *G01N 1/286* (2013.01); *G01N 1/2813* (2013.01); *G01N 2001/4094* (2013.01)

(58) Field of Classification Search
CPC ............................ G01N 1/286; G01N 1/2813
See application file for complete search history.

(56) References Cited

U.S. PATENT DOCUMENTS

| | | | |
|---|---|---|---|
| 6,948,843 B2 * | 9/2005 | Laugharn et al. ............. | 366/127 |
| 7,757,561 B2 | 7/2010 | Laugharn, Jr. et al. | |
| 8,082,041 B1 | 12/2011 | Radziemski | |
| 8,263,005 B2 * | 9/2012 | Laugharn et al. ............. | 422/128 |
| 9,080,167 B2 | 7/2015 | Laugharn, Jr. et al. | |
| 2002/0009015 A1 | 1/2002 | Laugharn, Jr. et al. | |
| 2002/0037359 A1 | 3/2002 | Mutz et al. | |
| 2006/0158956 A1 * | 7/2006 | Laugharn et al. ............. | 366/127 |
| 2012/0144905 A1 | 6/2012 | Laugharn, Jr. et al. | |

OTHER PUBLICATIONS

International Search Report and Written Opinion dated Oct. 16, 2014 from corresponding International Application No. PCT/US2014/041255.

* cited by examiner

*Primary Examiner* — Sam P Siefke
(74) *Attorney, Agent, or Firm* — Wolf, Greenfield & Sacks, P.C.

(57) ABSTRACT

Systems and methods for processing tissue samples using acoustic energy. The tissue sample may be collected and placed on a substrate (e.g., microscope slide), or other sample holder. A transfer substrate may be positioned on the other side of the sample opposite the substrate. A microscope incorporated with the acoustic treatment system may be used to view, identify and select a portion of the sample to be transferred from the initial substrate to the transfer substrate. The selected portion of the sample is exposed to focused acoustic energy while disposed between the two substrates. The focused acoustic energy has characteristics (e.g., high frequency, small focal zone) that may be effective to transfer the selected portion of the sample from the initial substrate to the transfer substrate. Such transfer may occur with little to no damage to the sample, for example, at low temperature isothermal conditions and/or little to no cavitation of or around the sample.

15 Claims, 9 Drawing Sheets

SYSTEMS AND METHODS FOR ACOUSTICALLY PROCESSING TISSUES SAMPLES

BACKGROUND

1. Field of the Invention

Systems and methods for processing samples with acoustic energy are generally disclosed.

2. Related Art

A number of methods exist for isolating a small (e.g., microscopic) amount of cells and/or tissue (e.g., histochemically stained) from a larger section of tissue. One popular method of isolation is laser capture microdissection. Laser capture microdissection involves the use of a laser (e.g., ultraviolet pulsed laser, infrared laser) in combination with a microscope, for identifying the region of tissue to be isolated, and focusing the laser onto certain portions of the tissue sample to "dissect" the identified region of tissue to be isolated, from the remaining tissue. The laser is positioned (e.g., by movement of the laser optics and/or the stage of the microscope) and focused in a manner so as to expose a region of cells and/or tissue of interest to the laser radiation.

Due to the application of laser radiation, the particular region of interest is separated from the remaining tissue, for example, by directly cutting the tissue and facilitating transfer of the selected region of interest from one surface to another. Transfer of tissue may occur through a number of ways, such as 1) by using the laser to make an incision that separates different regions of tissue; 2) by modulating the laser to generate a photonic force that propels a selected region of tissue off of the slide and toward a collecting container or substrate; 3) by relying on gravity to allow a separated region of tissue to fall into a collecting container or substrate; and/or 4) by using an adhesive material (e.g., membrane) to pick the separated region of tissue up from the original slide.

Laser capture microdissection has been used as a method of collecting selected cells for DNA, RNA and/or protein analyses, and is performed on a variety of tissue samples including blood smears, cytologic preparations, cell cultures and aliquots of solid tissue, frozen tissue, and formalin-fixed and paraffin embedded (FFPE) tissues. However the use of laser capture microdissection often results in an undesirable increase in radiation exposure, temperature and/or damage to the tissue that is isolated.

SUMMARY

The inventors have recognized and appreciated there to be advantages in using focused acoustic energy to transfer small portions (e.g., microscopic) of tissue and/or cells from a substrate, on which a tissue sample initially resides, to a transfer surface. Focused acoustic treatment may be effective to transfer a selected region of tissue sample from one substrate to another while allowing little to no alteration of, or damage to, the tissue upon transfer. In some embodiments, focused acoustic energy is used to facilitate tissue transfer under isothermal conditions, for example, so that the tissue sample may be maintained at a relatively low temperature during transfer, such as less than 50 C, room temperature, approximately 4 C, etc. In contrast, conventional methods used to transfer tissue sample from one substrate to another (e.g., laser capture microdissection) may result in undesirable heating and/or damage to the sample.

Certain parameters of focused acoustic energy, such as the frequency and the focal zone size, may be adjusted to suit the desired resolution of the region of the sample to be transferred. For example, transfer of a relatively small tissue sample may, in general, require high frequency acoustic energy (e.g., greater than 1 MHz) that converges so as to form a relatively small focal zone (e.g., having a width of less than 1 mm). Accordingly, a boundary surrounding a small region of tissue sample to be transferred may be traced out by a focal zone of acoustic energy so as to separate that particular region of tissue from the remaining sample. Alternatively, a focal zone of acoustic energy may cover a substantial region of the tissue to be transferred.

A substrate (e.g., microscope slide) supporting a tissue sample may be located adjacent to a transfer surface (e.g., surface of a collecting container, membrane, slide, etc.) such that the sample is sandwiched between the substrate and the transfer surface. At least a portion of the sample may be exposed to focused acoustic energy (originating from an acoustic energy source), causing transfer of the portion of the sample from the substrate to the transfer surface.

A system that incorporates a microscope apparatus or other imaging system appropriately calibrated with the acoustic energy source may be arranged to better accommodate such sample transfer. For instance, the relative position of the microscope apparatus and the acoustic energy source may be set such that the field of view of the microscope is coincident with the location at which the focal zone of acoustic energy is formed. Accordingly, various regions of the sample may be imaged using the microscope, at appropriate magnification(s), so as to identify the desired portion of the sample to be transferred from the substrate, using focused acoustics.

The system may be configured with appropriate control systems, e.g., including software, so that the portion of the sample that is desired to be transferred from the substrate may be selected, manually or automatically, according to the image(s) provided by the microscope. Such images may be provided by the viewfinder of the microscope itself, and/or may be displayed on a computer screen for a user and/or automated computer program to choose the portion of the sample to be transferred.

Acoustic energy may be focused at the location (e.g., within and/or around) of the selected portion of the sample. Exposure of the selected portion of the sample to the focused acoustic energy may cause the selected portion of the sample to be transferred from the initial substrate to a transfer surface. For example, the acoustic energy may serve to vibrate the sample to be dislodged from the substrate or otherwise cause an impedance mismatch at the interface between the substrate and the selected portion of the sample, and may further accommodate movement of the sample toward the transfer surface. Once the selected portion of the sample is transferred away from the substrate and toward the transfer surface, portions of the sample that were not selected for transfer remain on the substrate.

The focused acoustic energy may have a frequency of between about 100 kHz to 100 MHz and a focal zone having a width of less than about 2 cm. In some cases, to facilitate effective sample transfer, the focused acoustic energy may be suitably modulated to have a relatively high frequency, of between about 0.1 MHz and about 3 MHz, and a relatively small focal zone, for example, having a width of less than about 1 cm, or less than about 1 mm. Further, the acoustic energy may have certain characteristics such that upon exposure of the sample to the acoustic energy, cavitation does not occur, minimizing the potential for the sample to be damaged.

In an illustrative embodiment, a method of processing a sample is provided. The method includes providing a substrate supporting a tissue sample; positioning a transfer surface adjacent to the substrate such that the sample is disposed between the substrate and the transfer surface; and transferring at least a portion of the sample from the substrate to the transfer surface by exposing the portion of the sample to focused acoustic energy having a frequency of about 100 kHz to 100 MHz generated from an acoustic energy source.

In another illustrative embodiment, an acoustic treatment apparatus is provided. The apparatus includes a substrate for supporting a tissue sample; a transfer surface adapted to be positioned adjacent to the substrate such that the sample is disposed between the substrate and the transfer surface; an acoustic energy source configured to provide focused acoustic energy having a frequency of about 100 kHz to 100 MHz to the sample while the sample is supported by the substrate to cause transfer of at least a portion of the sample from the substrate to the transfer surface; and a substrate holder arranged to position the substrate such that the sample is located at least partially in a focal zone of the acoustic energy during transfer of the portion of the sample.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

Aspects of the invention are not limited in application to the details of construction and the arrangement of components set forth in the following description or illustrated in the drawings. Other embodiments may be employed and aspects of the invention may be practiced or be carried out in various ways. Also, aspects of the invention may be used alone or in any suitable combination with each other. Thus, the phraseology and terminology used herein is for the purpose of description and should not be regarded as limiting.

Focused acoustic treatment, optionally coupled with microscopy or other imaging, may be used to facilitate transfer of small sections of tissue (e.g., biological material, cells, connective tissue, hard tissue, soft tissue, etc.) from one surface to another. By using focused acoustic energy, the transferred tissue remains, for the most part, structurally, chemically and biologically unaltered, except for the fact that the tissue is moved from one substrate to another. That is, upon transfer, the acoustic energy, in general, does not cause any appreciable biological or chemical alteration, degradation or damage, to the tissue. Any such alteration is minimal compared with traditional methods of tissue transfer, such as through a direct physical transfer (e.g., use of an adhesive peel or attachment, tweezers, scalpel, etc.) or laser capture microdissection. Accordingly, the portion of the tissue sample that is transferred using focused acoustics may be suitably analyzed or otherwise processed, as desired, with relatively minimal alteration to the tissue. Of course, such minimal effect on a transferred tissue sample is not required in all embodiments. For example, some systems in an accordance with illustrative embodiments of the invention may be used to select and transfer tissue samples that are to be disrupted in a significant way, e.g., by homogenization, and thus minimal alteration of the sample during transfer need not be required.

Also, systems of the present disclosure may be used for other additional types of focused acoustic processing of a sample, such as for mixing or DNA/RNA shearing, e.g., to reduce the base pair length of DNA fragments from 1,000s or 10,000s of base pairs to lengths of 3 k base pairs or smaller, in a reproducible and high-yield manner. Examples of such acoustic treatment systems and control arrangements are described in U.S. Pat. Nos. 6,948,843 and 6,719,449, assigned to Covaris of Woburn, Mass., and may be incorporated in systems described herein.

In some embodiments, the use of focused acoustic energy to cause tissue sample transfer from one substrate to another allows for appropriate temperature control of the tissue during transfer. In some instances, because focused acoustic processing may be controlled to occur isothermally, the temperature of the tissue sample, and its surrounding region, may be tightly regulated. For example, as discussed above, focused acoustic energy may be used to transfer at least a portion of a tissue sample from one substrate to another while maintained within a desired temperature range, such as at a relatively low temperature (e.g., less than 50 C, room temperature, approximately 4 C, etc.). In contrast, tissue sample transfer that is caused by traditional methods, such as laser capture microdissection, often results in undesirable, and uncontrolled, heating of the sample, or at least portions of the sample.

As discussed, the use of focused acoustic energy to transfer a tissue sample between substrates may not alter or damage the morphology and chemistry of the tissue sample transferred, nor are surrounding tissue/cells altered or damaged. Accordingly, methods presented herein are useful for collecting selected tissue/cells for DNA, RNA and/or protein analyses, which may originate from any of a variety of types of tissue samples, including blood smears, cytologic preparations, cell cultures, aliquots of solid tissue, and other sources.

Sections of tissue/cells for use with systems described herein may be appropriately frozen, fixed and/or embedded. FFPE (formalin fixed, paraffin embedded) tissue types, amongst others, allow for extended storage of the samples with relatively little degradation of DNA, RNA, proteins or other materials in the sample. Thus, after an appropriate period of time (e.g., could be days, weeks, months, years, etc.), the archived tissue sample may be placed on a substrate, such as a microscope slide, for magnified visualization of the sample. Based on the field of view provided by a microscope, a user and/or automated computer software program may select a particular region of the sample to be transferred to another substrate, for example, chosen for further processing or analysis. The selected region of the sample may be exposed to focused acoustic energy having appropriate characteristics so as to cause transfer of the selected region from one substrate to another, for subsequent analysis and/or processing.

As discussed, portions of frozen and paraffin embedded archival tissue may be transferred between substrates using focused acoustics, without damage or alteration. Examples of paraffin embedded tissue samples and acoustic processing thereof are described in U.S. application Ser. No. 13/678,755, entitled "System and Method for Processing Paraffin Embedded Samples," assigned to Covaris of Woburn, Mass., and may be incorporated in systems described herein.

Figure 1:
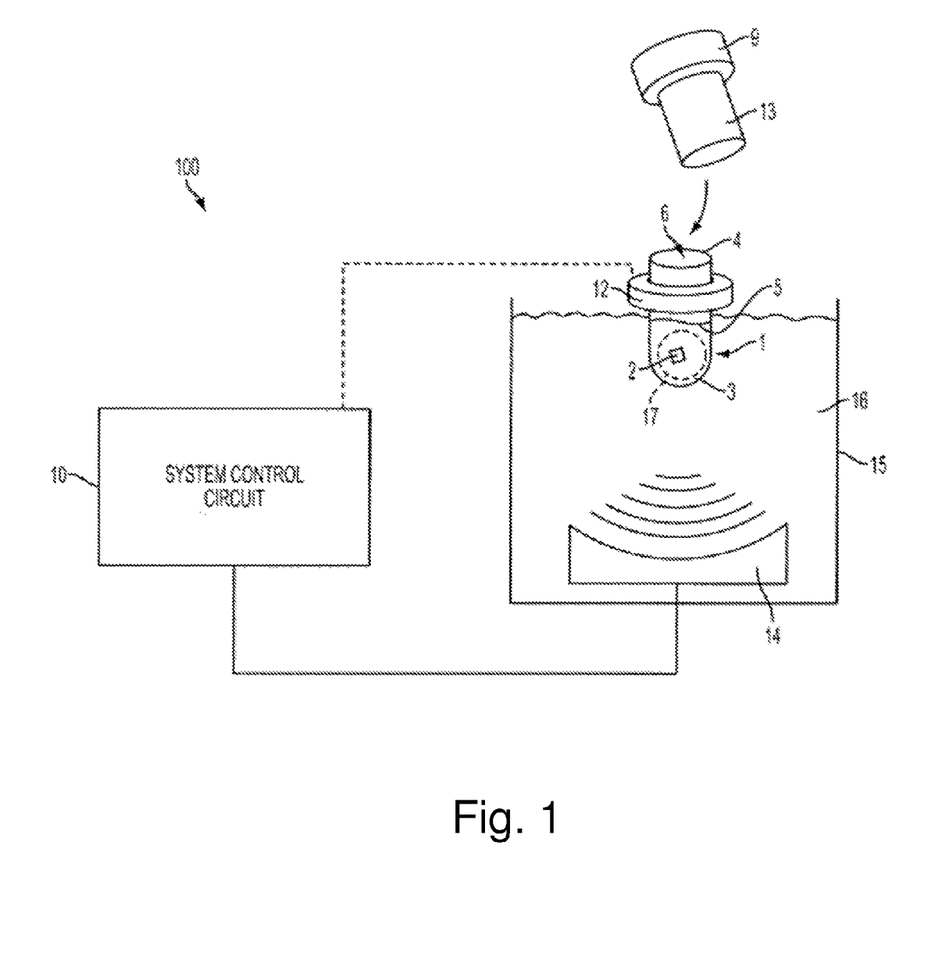
FIG. 1 shows a schematic block diagram of an acoustic treatment apparatus.

FIG. 1 shows a schematic block diagram of an acoustic treatment system 100 that incorporates various features that may be used with one or more aspects of the invention. It should be understood that although embodiments described herein may include some or all aspects of the invention, aspects of the invention may be used alone or in any suitable combination with other aspects of the invention.

In the illustrative embodiment shown in FIG. 1, the acoustic treatment system 100 includes an acoustic transducer 14 (e.g., including one or more piezoelectric elements) that is capable of generating an acoustic field (e.g., converging at a focal zone 17) suitable to cause mixing, vibration and/or other effects in a sample 1 held by a sample holder 4. While the sample holder 4 is shown in this embodiment to be a vessel (e.g., test tube, vial) that contains the sample 1, it can be appreciated that other sample holders and/or substrates may be used to hold or otherwise support the sample 1, as described further below.

The acoustic transducer 14 may produce acoustic energy within a frequency range of between about 100 kilohertz and about 100 megahertz such that the focal zone 17 has a width of about 2 centimeters or less. When formed, the focal zone 17 of the acoustic energy may be any suitable shape, such as spherical, ellipsoidal, rod-shaped, line-shaped, cigar-shaped, or column-shaped, for example, and may be positioned at least partially where the sample 1 is located. For instance, the transducer may have a curvature (e.g., dome, hemispherical, cylindrical, semi-cylindrical), or may otherwise be shaped or positioned in conjunction with a focusing element (e.g., lens, acoustic filter) that causes the formation of a particular pattern or shape of acoustic energy. In some embodiments, the transducer may be formed of a piezoelectric material, such as a piezoelectric ceramic. The focal zone 17 may be larger than the sample, or may be smaller than the sample, as shown in FIG. 1, e.g., the focal zone 17 may fit entirely within the sample holder 4. U.S. Pat. Nos. 6,948,843 and 6,719,449 are incorporated by reference herein for details regarding the construction and operation of an acoustic transducer and its control.

The sample holder 4 may have any suitable shape, size, material, or other arrangement/feature. While the sample holder is depicted as an enclosable container (e.g., glass tube, plastic container, well in a microtiter plate, plastic vial, vessel, 6×16 mm glass or plastic tube (approximately 150 microliter volume) having a screw cap, etc.) that may be supported at a location by a holder support 12, it can be appreciated that certain types of sample holders other than that shown may be used. For example, the sample holder 4 may be a cylindrical tube with a flat bottom and a threaded top end to receive a cap 9, may include a cylindrical collar with a depending flexible bag-like portion to hold a sample, may be a single well in a multiwell plate, may be a microscope slide, may be a cube-shaped sample holder, and/or may be of any other suitable arrangement.

The sample holder may be, or may otherwise include, a substrate for supporting a sample to be transferred to a surface of another substrate. In some embodiments, where a sample holder may include an enclosed space for containing a sample (e.g., test tube, vial), a transfer substrate may extend within the enclosed space in a manner that allows for the tissue sample to be in close proximity to the surface to which the sample is transferred. As discussed and shown further below, a sample holder may be, or may include, a relatively flat substrate having a surface on which the sample may rest, such as that provided by a microscope slide or other suitable substrate.

In some embodiments, an initial substrate on which a sample is supported is not required for transfer of a portion of the sample to a transfer substrate. For example, focused acoustic treatment may cause transfer of a free-floating portion of a tissue sample in a liquid from the liquid to a suitable transfer substrate.

Sample holders and/or substrates described herein may be formed of glass, plastic, metal, composites, and/or any suitable combinations of materials, and may be formed by any suitable process, such as molding, machining, stamping, and/or a combination of processes.

The illustrative embodiment of FIG. 1 further shows the sample 1 to include a solid material 2, such as a tissue sample that has been formalin fixed and paraffin embedded (i.e., an FFPE sample) that is contained in a sample holder 4 along with a liquid 3, e.g., a non-solvent aqueous solution. The liquid 3 may be a mixture of water and detergent (e.g., 0.25% sodium dodecyl sulfate solution), although other solutions (solvent or non-solvent) are possible, or no solution at all.

The sample may have any suitable volume and/or mass, e.g., the sample may be a so-called "scroll" or piece of FFPE tissue microtome sliced from a larger sample piece, a tissue sample taken by needle biopsy, or a sample produced by any other suitable method. In some embodiments, a sample cut by microtome may have a thickness of about 5 to 25 microns and a length of 30 mm or less. For example, a sample may be sized to have a volume of about 4 cubic millimeters or less. Depending on the application or sample involved, other volumes may be used, such as a volume of less than 10 cubic millimeters, less than 30 cubic millimeters, less than 50 cubic millimeters, less than 100 cubic millimeters, or less than 500 cubic millimeters.

In some cases, care may be taken to suitably define a headspace 6 (shown to be a gaseous region immediately above the air-liquid interface 5) in the sample holder 4 prior to acoustic treatment. Accordingly, the cap 9 may include a lower portion, or extension 13, that reaches down into the space defined by the vessel.

Though, in some embodiments, the extension 13, or a portion thereof, may be provided as a transfer substrate that extends within the space defined by the vessel in a manner that allows for the sample to be in close proximity to a surface to which the sample is transferred. Accordingly, the extension may reach into the enclosed vessel toward the sample, which, in some instances, may be through a liquid 3. That is, tissue sample transfer from one substrate to another, facilitated by focused acoustics, may occur in a wet environment, or alternatively, may occur in a dry environment. In some embodiments, the extension includes a component (e.g., metal, plastic, glass, ceramic disc) or other appropriate member that provides a suitable surface to which a portion of the sample may be transferred.

In this illustrative embodiment, as discussed, the sample holder 4 may be associated with a holder support 12 (e.g., molded integrally, attached, welded, or removably attached) that helps support the holder 4 during acoustic treatment. The holder support 12 may take any suitable arrangement or location, such as a ring-shaped element that is fixed relative to the vessel, as shown in FIG. 1. While embodiments described herein do not necessarily require a holder support 12, such a holder support 12 may serve to interface with the acoustic processing device so that the sample holder 4 and the sample itself may be positioned at a known location for processing/analysis, and relative to an acoustic field.

The holder support 12 is not limited to a device like that shown in FIG. 1, and may be constructed in a manner such that the holder support does not enclose a space. It can be appreciated that a holder support may function as a support for any suitable substrate. Holder supports may serve to appropriately position other types of sample holders and may include a rack, slot, tray, gripper element, platform, recessed area, clamp, box or any other suitable arrangement for holding and/or moving a sample holder and/or substrate with respect to a focal zone 17 and/or a microscope apparatus.

Figure 2:
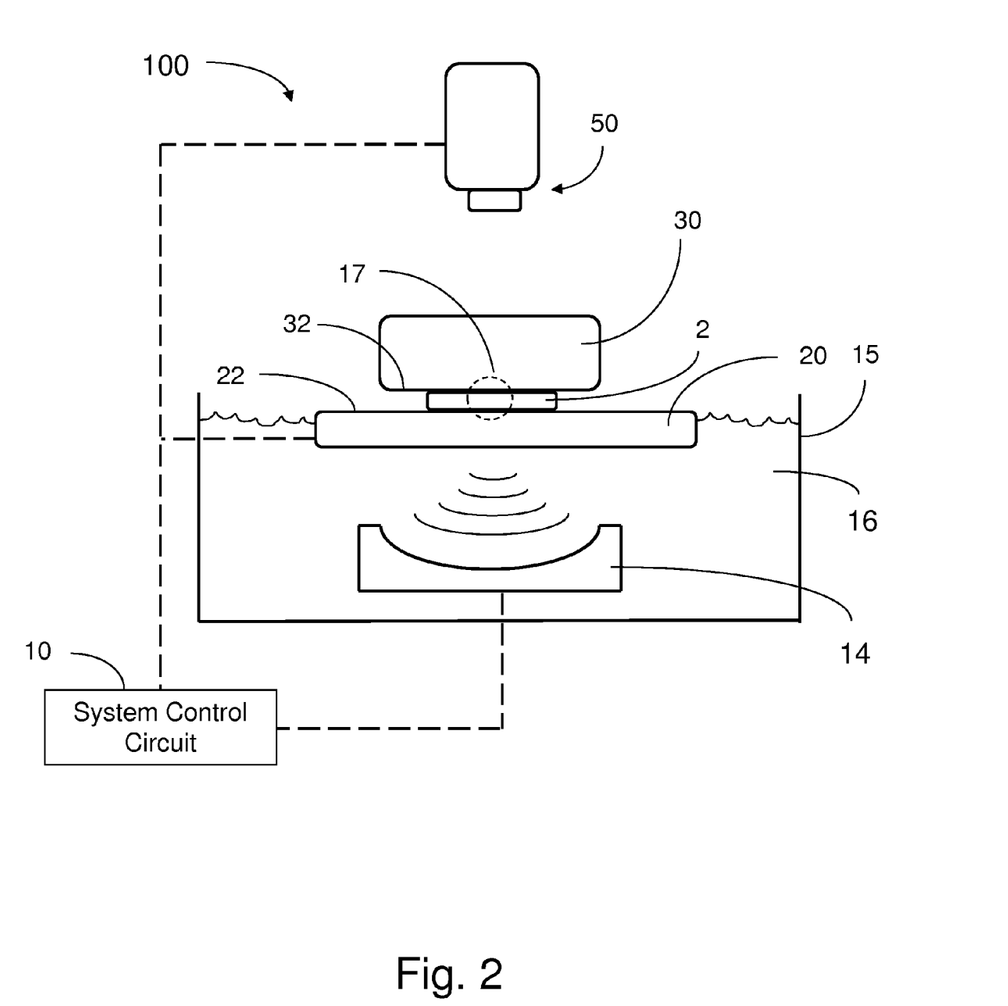
FIG. 2 illustrates a schematic of an acoustic treatment apparatus in accordance with some embodiments.
Figure 3:
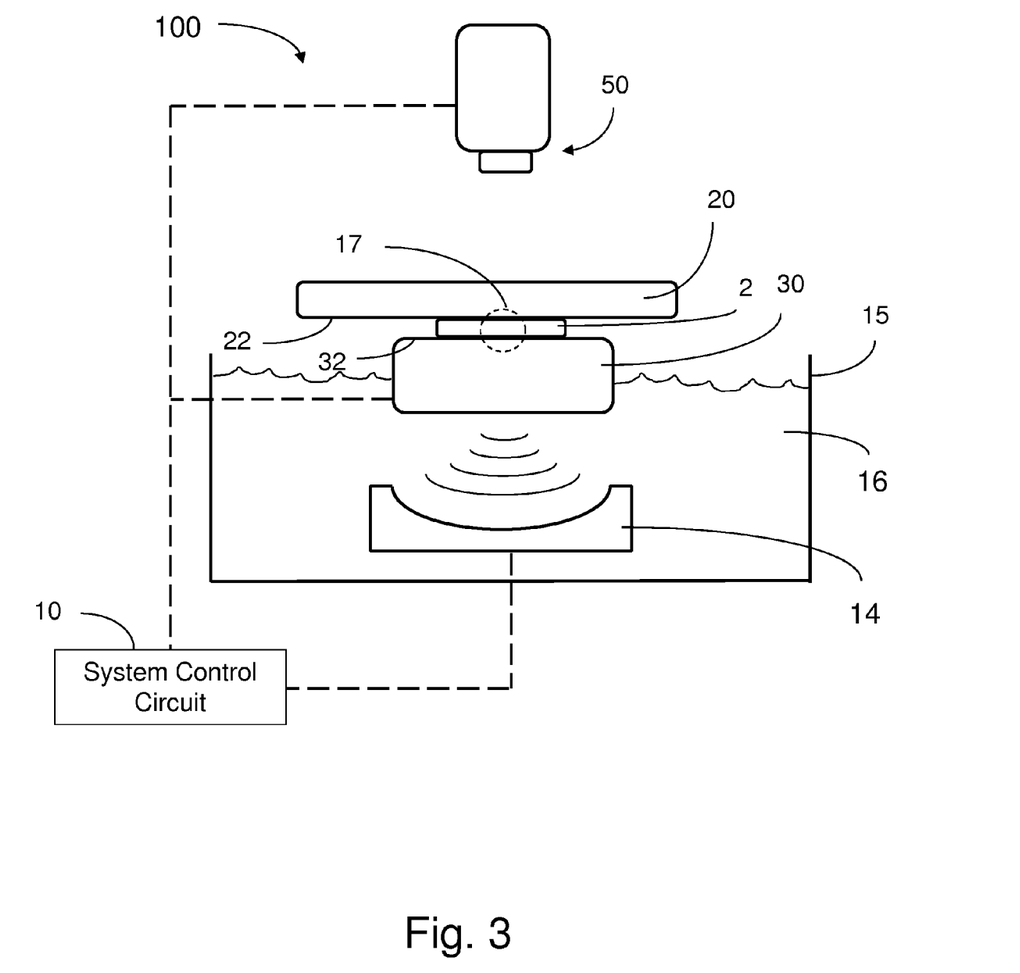
FIG. 3 depicts a schematic of another acoustic treatment apparatus in accordance with some embodiments.

As noted above, the sample holder may be provided as an initial substrate (e.g., microscope slide), such as that shown in FIGS. 2-3, suitable for supporting a tissue sample. The sample may be adhered, or otherwise attached, to a surface of the substrate (e.g., on top of the substrate, or in an inverted position), or may simply rest on the substrate without requiring use of an attachment or adhesive material. In some embodiments, the substrate may include a recessed area (not expressly shown in the figures) for receiving the sample and, in some cases, that substantially maintains the sample at a desired location relative to the substrate. For instance, such a recess may have borders/walls that substantially prevent the sample from drifting or otherwise moving off of a particular position on the substrate.

The acoustic treatment system 100 may also include a coupling medium container 15 that is capable of holding a medium 16, such as water or another liquid, gas (e.g., air, inert gas), gel (e.g., silicone), solid (e.g., elastomeric material), semi-solid, and/or a combination of such components, which transmits acoustic energy from the transducer 14 to the initial substrate 20.

In embodiments where the medium 16 includes a solid or semi-solid, or is otherwise able to retain its shape, a container 15 need not be provided, or a portion of the medium 16 itself may function as a container 15, e.g., to hold a liquid or gas portion of the medium 16. For example, in one embodiment, the transducer 14 may be attached to a solid coupling medium 16 (such as a silica or silicone material), which is also attached to a holder support 12, which may be formed, at least in part, by an opening or other feature of the medium 16. Thus, the transducer 14, medium 16 and holder support 12 may be formed as a single integrated part, if desired.

Due to the isothermal nature of the focused acoustic treatment, during acoustic processing, the temperature of the coupling medium may be maintained, without substantial fluctuation, as opposed to temperature changes that may otherwise occur from other methods of sample transfer. In some embodiments, the temperature of the coupling medium is maintained at a relatively low temperature, e.g., 40-60 degrees C., although thermal control at lower or higher temperatures are also possible. Accordingly, during sample transfer (i.e., during focused acoustic treatment), in keeping with the temperature of the coupling medium being maintained to be relatively constant, the portion of the sample that is transferred, or the entire sample itself, may also be maintained at a relatively low temperature, e.g., does not exceed a temperature of 40-60 degrees C.

As alluded to above, in some embodiments, during transfer, the sample is maintained in a wet environment. For example, the sample is kept in the presence of a liquid (e.g., aqueous, non-aqueous) solution when focused acoustic energy is applied to the sample. Despite the presence of the liquid, the focused acoustic energy facilitates transfer of the selected portion of the sample from the initial substrate to the transfer substrate.

Alternatively, the sample may be maintained in a relatively dry environment during transfer. For instance, the sample is kept dry during exposure to focused acoustic energy, which may also facilitate transfer of the selected portion of the sample from the initial substrate to the transfer substrate.

In some embodiments, for paraffin embedded samples, focused acoustic energy may be used to remove (or disassociate) paraffin from the tissue sample. Such removal may occur with or without hydration of the sample. Certain types of surfaces and substrates may promote, or exclude, transfer of the portion of the sample. Such transfer of a paraffin embedded sample may occur in a substantially dry environment, or a substantially wet environment. A substantially wet environment may provide for the ability for the sample to be rehydrated, with or without the presence of staining (e.g., immunohistochemical staining).

In some embodiments, appropriate parameters of the acoustic treatment system may be controlled, such as certain characteristics of the acoustic field and/or the relative position of the acoustic transducer 14 and the initial substrate 20 (e.g., by moving the transducer and/or the substrate support). Accordingly, during acoustic processing, the sample may be positioned at a desired location relative to an appropriate focal zone 17. The transducer 14 may produce the focused acoustic energy to have a particular size and shape so that the focal zone is suitably positioned relative to the sample or initial substrate.

To control the acoustic transducer 14, the acoustic treatment system 100 may include a system control circuit 10 that controls various functions of the system 100 including operation of the acoustic transducer 14, positioning of the initial substrate, and operation of a microscope apparatus 50 configured to image the sample. The system control circuit 10 may provide control signals to a load current control circuit, which controls a load current in a winding of a transformer. Based on the load current, the transformer may output a drive signal to a matching network, which is coupled to the acoustic transducer 14 and provides suitable signal(s) for the transducer 14 to produce desired acoustic energy.

As discussed in more detail below, the system control circuit 10 may control various other functions of the acoustic treatment system 100, such as positioning of an initial substrate 20 and/or acoustic transducer 14. For instance, the figures show a dashed line linking the control circuit 10 to the holder support 12, schematically representing an optional positioning system, e.g., which may include a robot, gantry, screw drive, or other arrangement to move the holder support 12. The system control circuit 10 may be configured to receive operator input, such as commands for system operation, or automatically provide input. The system control circuit 10 may output appropriate information in a suitable manner (e.g., to a visible display screen, as indicator lights, etc.). Such information may include sample treatment status information in electronic data form, suggestions/recommendations for applying further acoustic treatment, or other information that may be made available.

FIG. 2 schematically depicts an embodiment where an initial substrate 20 (e.g., microscope slide, culture dish, portion of a vessel/container/tube, etc.) includes a surface 22 upon which a tissue sample 2 resides, or to which the sample is adhered or attached. In some embodiments, while not expressly shown in the figures, the initial substrate may be located within, or is a part of, a sample holder such as a test tube or vessel.

The substrate may include a recessed area (also not expressly shown in the figures) in which the sample may at least partially reside, preventing any undesired drift or movement of the sample relative to the substrate. In some embodiments, the initial substrate is suited to hold a plurality of tissue samples. For example, an initial substrate and/or substrate support may include a rack, carousel, array, or other suitable arrangement for presenting a large number of tissue samples for focused acoustic processing, in a convenient and high-throughput manner.

As further shown, the surface 22 of the initial substrate 20 that supports the sample 2 is also located adjacent to a (sample-facing) surface 32 of a transfer substrate 30. The transfer substrate may include any suitable surface or area that serves to collect and maintain the tissue sample in place upon transfer, for further analysis or processing (e.g., microscope slide, pad or other appropriate collecting container). In some embodiments, the transfer substrate may extend from and/or may be a part of a cap for engaging with an appropriate sample holder.

The transfer substrate may include any suitable material, for example, glass, metal, polymer, fabric, or suitable combinations thereof. In some embodiments, the transfer substrate 30 and the initial substrate 20 are similar in construction (e.g., both are microscope slides, similar or different in shape), or may have appreciable differences.

While not shown in the figures, the initial substrate and/or the transfer substrate may be held in place, manipulated or otherwise supported directly or indirectly by a substrate holder (e.g., clamp, adhesive, robotic arm, etc.). For example, a substrate holder may hold the initial substrate and/or the transfer substrate, or may hold a sample holder that includes an initial substrate and/or transfer substrate.

In some embodiments, the surface 32 of the transfer substrate 30 may include an adhesive, additive, or other suitable agent, that facilitates transfer of the sample to the surface of the transfer substrate when subject to appropriate acoustic energy. Though, it can be appreciated that the additional agent(s) may not be necessary for suitable relocation of the sample to the transfer substrate to occur. For example, the surface of the transfer substrate may naturally be adapted to facilitate (e.g., via electrostatic attraction, cohesion, etc.) transfer of a portion of the sample from the initial substrate 20 (e.g., by being dislodged or separated from the substrate) to the surface of the transfer substrate 30.

As further shown in FIGS. 2-3, the acoustic treatment system 100 may incorporate a microscope apparatus 50 for imaging particular regions of the sample at a preferred magnification while located on, adhered and/or attached to, the initial substrate 20.

In some embodiments, while not required, the initial substrate and/or the transfer substrate is transparent or translucent, which may allow the microscope to provide a suitable magnified view of the portion of the sample through the substrate(s).

Alternatively, in some embodiments, the initial substrate and/or the transfer substrate may be optically opaque. For example, the sample may be imaged while located on the initial substrate 20 before the transfer substrate 30 is applied to the sample. The region of the sample to be transferred may be optionally programmed into the system and stored in memory for later exposure to focused acoustic energy, as discussed further below. Accordingly, once the selected region is properly programmed or stored in memory, other regions of the sample may be imaged or otherwise analyzed/processed. At an appropriate time, the transfer substrate may be applied or positioned adjacent (e.g., attached) to the initial substrate. Once the appropriate information regarding the sample (and the selected region) is retrieved, the sample may then be subject to focused acoustic energy, resulting in suitable transfer of the selected portion of sample to the transfer substrate. It can be appreciated that the system may be configured so that any or all of the above steps may be performed automatically.

The microscope may incorporate any suitable imaging modality, such as traditional optical microscopy, fluorescence microscopy, bright field microscopy, differential interference contrast microscopy, phase contrast microscopy, etc. In some embodiments, an imaging device other than a microscope may be used. The microscope apparatus 50, which may be a part of a microscope, may be used to view a tissue sample having individual cells or clusters of cells, for identification and selection of one or more regions of the tissue sample for isolation/separation/transfer. In some cases, the microscope apparatus 50 is optionally configured to view regions of the sample located underneath the surface, within the bulk of the sample.

To accommodate selection of a portion of the sample to be transferred from one substrate to another, the system control circuit 10 may control operation of the acoustic transducer 14 in cooperation with the microscope apparatus 50, where such operation occurs manually, partially automatically (where some steps are manual and some steps are automatic) or entirely automatically. Further, the microscope apparatus 50 may be appropriately calibrated with the acoustic transducer 14 and the initial substrate 20 such that the field of view of the microscope is coincident with the location at which the focal zone 17 of acoustic energy may be formed. Accordingly, the microscope apparatus 50 may provide an image to a user, or to an automated software program, that assists in identifying the portion of the sample 2 that is desired to be transferred, using focused acoustics, from the initial substrate 20 and to the transfer substrate 30. Such an image may be output, for example, to a display monitor through the control system and/or a microscope viewfinder.

Once the image is reviewed, a portion of the sample may be selected to be transferred, for example, by digitally tracing out a boundary or otherwise selecting a region of the sample that is to be transferred from the initial substrate and to the transfer substrate. In some embodiments, based on suitable calibration of the system, when it is desired for the selected portion of the sample to be transferred, the relative position of the initial substrate and the transducer may be adjusted so that the appropriate region(s) of the sample may be exposed to acoustic energy having suitable characteristics (e.g., focal zone size, location, parameters, etc.), to result in the desired sample transfer. For instance, a user may look into the viewfinder of the microscope and determine the particular section of the sample to which focused acoustic energy is to be applied. The position of that particular section may then be adjusted relative to the transducer such that the selected sample section may be appropriately exposed to acoustic energy having the desired characteristics.

In some embodiments, data that records information regarding the selected portion of the sample (e.g., location on the sample, shape/size of the selected portion, acoustic energy characteristics that would cause the selected portion to be separated from the rest of the sample, etc.) may be stored in memory of the acoustic treatment system 100, for future reference. For example, such data may include information regarding multiple selected locations of a sample to be transferred, and/or information regarding multiple samples. When it is desired for one or more samples, or portions of the sample(s), to be transferred from one substrate to another, data corresponding to the selected portion(s) of the sample(s) may be retrieved from memory and read/used by the acoustic treatment system. Such data may provide guidance for the acoustic treatment system to control the relative position of the transducer and the sample(s) for appropriate exposure of the selected portion(s) of the sample(s) to acoustic energy, for resulting transfer.

It can be appreciated that any or all of the processes described herein (e.g., selection of the portion of the sample to be transferred, setting appropriate parameters of focused acoustic energy, positioning the sample relative to the acoustic transducer, exposing the sample to focused acoustic energy, etc.) may be performed manually or automatically. For example, certain regions of an image of a sample viewed using a microscope, according to embodiments described herein, may be readily identifiable through automated image processing techniques (e.g., regions that exhibit fluorescence). It may be desirable that these regions be transferred to another substrate for further analysis. Thus, the system may run an appropriate software routine that automatically selects such regions of the sample for subsequent transfer. The system may further determine the acoustic characteristics necessary for the desired transfer of the particular portion of tissue sample(s) to occur (e.g., based on the type of sample to be processed), and may adjust the transducer parameters (e.g., location, power output, cycles per burst, etc.) accordingly. The system may automatically carry out the transfer by suitably positioning the sample and the transducer relative to one another, and operating the transducer to generate an appropriate focal zone 17 of acoustic energy at the selected region(s) of the sample. Or alternatively, a user may manually control the system to execute any, or every, one of the above-noted steps.

As further shown in FIG. 2, the sample 2 resides on the initial substrate 20, yet is sandwiched between the initial substrate 20 and the transfer substrate 30. As discussed herein, a particular portion, or portions, of the sample may be selected to be displaced from the surface of the initial substrate 20 and transferred on to the surface of the transfer substrate 30. Accordingly, while the sample is disposed between the initial substrate 20 and the transfer substrate 30, the sample 2 is selectively exposed at appropriate locations to a focal zone 17 of acoustic energy generated by an acoustic transducer 14. In some embodiments, and as shown, the transducer 14 transmits acoustic energy through a coupling medium 16 (e.g., water) and through the substrate 20 (e.g., glass slide), toward the sample 2, so as to create the focal zone 17.

Exposure of the sample to the focal zone 17 may be controlled in accordance with the portion(s) of the sample that are chosen for transfer. Such exposure of the sample 2 to the acoustic energy at the focal zone 17 may result in any of a number of various effects. For example, as discussed previously, the focused acoustic energy may cause vibration of the selected portion of the sample while on the initial substrate, may create an impedance mismatch at the interface between the selected portion of the sample and the initial substrate, or may give rise to other suitable acoustic effect(s). Such effect(s) may cause the selected portion of the sample to be, at least partially, dislodged, separated, cut or otherwise kinetically driven from the substrate 20 and transferred to the transfer surface 32.

The separated portion of the sample may be kinetically driven to the transfer surface 32 in any suitable manner. In some embodiments, the acoustic energy applied to the sample may cause the separated portion to move or otherwise be propelled toward the transfer surface. Accordingly, the acoustic energy may cause the sample, or fluid mixed with the sample, to move rapidly or be displaced, for example, by acoustic streaming, heating, vibration, or another suitable mechanism, that results in transfer of the selected portion of the sample to the transfer substrate, while experiencing minimal damage or disruption to the sample itself.

As discussed above, in some embodiments, transfer of the sample may occur in a substantially dry environment. For instance, for a dry paraffin embedded sample that is to be transferred, upon activation of the acoustic system, the focused acoustic field travels through the initial substrate (e.g., glass slide) and toward the sample. Upon departure from the initial substrate, the focused acoustic field immediately encounters an impedance mismatch, for example, at an interface between glass and paraffin. In this example, the acoustic energy effectively softens the paraffin and the paraffin/sample is pushed in a direction (e.g., upward away from the transducer) toward the transfer substrate 30 (e.g., transfer pad). As the paraffin/sample lifts off the initial substrate 20, an air gap is created. This air gap creates an acoustic interface that reflects subsequent high frequency acoustic energy back toward the transducer. Such acoustic reflection allows the sample to be transferred using only a small amount of energy and, hence, with minimal damage/disruption, to the sample.

In some embodiments, the initial substrate 20 may be positioned with the sample so that substantially any or all focused acoustic energy to which the sample is exposed is concentrated at the desired region of the sample to be transferred. For example, the initial substrate 20 may be positioned just above the coupling medium 16 (e.g., 2-3 mm), creating a liquid/water interface that serves to reflect extraneous acoustic energy away from the sample. Accordingly, the sample is exposed to acoustic energy only upon activation of the focused acoustic system; and further, unfocused acoustic energy (e.g., acoustic sidelobes) is reflected away from particular regions of the sample where it is only desired that a focal zone of acoustic energy be present. For a partially spherical shaped transducer, when the initial substrate is elevated to a position slightly above the surface of the coupling medium (e.g., water), desired portions of the sample are exposed to the focal zone of a cone-shaped acoustic field, while sidelobes of the acoustic field are reflected back at the liquid/air interface.

Such methods of transferring the sample from one substrate to another using acoustic energy provides for an enhanced level of control of thermal energy between the sample and its environment. Once transfer of the appropriate portion of the sample is complete, the transfer substrate 30 and the transferred portion of the sample may be removed from the system for further processing and/or analysis.

It can be appreciated that transfer of a sample from an initial substrate 20 to a transfer substrate 30 does not require microscopy imaging. In some embodiments, an entire sample, or a significant portion thereof, may be transferred from one substrate to another. For instance, a partially cylindrical transducer adapted to generate a line-shaped focal zone of acoustic energy may be used through an acoustic raster scan to transfer an entire sample, or the entirety of a sample up to a certain point, from one substrate to another, without need for microscopy.

In an embodiment, adjacent scroll samples may be cut from a tissue sample block using a microtome. It may be desired that different samples along the scroll be subject to certain types of analyses. For example, the first and third samples along the scroll may be transferred to a slide that is sent for histological analysis; and the second sample along the scroll may similarly be transferred to a slide that is sent for molecular analysis (e.g., AFA transferred for biomarker, sequencing, qPCR, SNP).

FIG. 3 depicts another illustrative embodiment that is similar in configuration to the embodiment shown in FIG. 2, except the initial substrate 20 and the transfer substrate 30 are oppositely positioned. That is, the tissue sample 2 is located between the initial substrate 20 and the transfer substrate 30, yet the initial substrate and transfer substrate are inverted in comparison to the system shown in FIG. 2. Accordingly, the transducer 14 transmits acoustic energy through the coupling medium 16, through the transfer substrate 30, and toward the sample 2.

In some cases, the embodiment depicted in FIG. 3 may be used for gravity-assisted microdissection, where focused acoustic energy is used to facilitate or cause separation of a portion of the tissue sample 2 from the initial substrate 20 (e.g., by vibrating a selected portion of the sample off of the surface of the initial substrate) and leaving an unselected portion of the sample to remain on the initial substrate. The separated portion of the sample then falls by force of gravity on to the surface of the transfer substrate, and on which the separated portion of the sample will subsequently reside. After the selected portion of the sample is appropriately transferred, the transfer substrate together with the transferred portion of the sample may be removed from the system for additional processing and/or analysis.

As discussed, in some embodiments, the emitted acoustic energy has a frequency of between about 100 kilohertz and about 100 megahertz, and generates a focal zone having a width of less than about 2 centimeters. As discussed and shown herein, for sample holders that include appropriate containers and/or substrates, the acoustic energy may originate from an acoustic energy source spaced from and exterior to the sample holder, e.g., the acoustic energy may pass through a coupling medium to the sample holder such that at least a portion of the acoustic energy propagates exterior to the sample holder. In some cases, a peak incident power level of the acoustic energy may be about 175 watts, although other power levels, such as between 100 and 400 watts, may be used.

Though, in some cases, more effective sample transfer occurs when the focused acoustic energy has a relatively high frequency and/or a small focal zone. In some embodiments, the frequency of focused acoustic energy for causing sample transfer from one substrate to another may range between about 0.05 MHz and about 5 MHz, between about 0.1 MHz and about 3 MHz, between about 0.1 MHz and about 1 MHz (e.g., ~0.5 MHz), between about 1 MHz and about 1.5 MHz (e.g., ~1.1 MHz), between about 2 MHz and about 3 MHz (e.g., ~2.5 MHz).

The focal zone of the acoustic energy may be of an appropriate size so that a suitable amount of tissue can be transferred, at a desired resolution, for subsequent processing/analysis (e.g., biological, chemical, molecular, etc.). In some embodiments, the size (e.g., width, diameter) of the focal zone of acoustic energy may be less than about 1 cm (e.g., ~8 mm), less than about 5 mm (e.g., ~2 mm), less than about 1 mm, less than about 500 microns, or less than about 100 microns.

In general, while not in all cases, the higher the frequency of acoustic energy emitted, the smaller is the resulting focal zone produced. For example, for some configurations of acoustic treatment systems, focused acoustic energy emitted at ~1.1 MHz may give rise to a focal zone having a diameter of ~2 mm, or focused acoustic energy emitted at ~0.5 MHz may result in a focal zone having a diameter of ~8 mm. Or, in some cases, focused acoustic energy emitted at ~2.5 MHz may give rise to a focal zone having a diameter of less than 1 mm.

In an embodiment where the acoustic treatment system 100 includes an acoustic treatment apparatus from a Covaris S230 or E230 model, acoustic treatment may be applied or otherwise configured to use a 10-30% duty cycle, a peak incident power of 100-300 watts, 100-300 cycles per burst for about 10-150 seconds. Of course, other duty cycles, peak power, cycles per burst and/or time periods may be used. In some embodiments, the coupling medium 16, which may be water, may be kept at a temperature of 40-60 degrees C. during the sample transfer.

Tissue samples may be prepared by any suitable manner. The tissue may be relatively soft tissue or hard tissue. In some cases, before mounting on a sample holder and/or initial substrate, the tissue sample may be subject to any suitable treatment, for example, filtration, staining, fixing, embedding, purification, etc. For instance, as discussed above, the tissue sample may be fixed (e.g., with formalin and/or paraffin) so as to prevent decay or degradation, allowing for preservation/stabilization of the tissue for analysis/examination. A fixation agent may be used to protect the tissue sample from damage, for example, by disabling intrinsic biomolecules, such as proteolytic enzymes which may otherwise lead to digestion or degradation of the sample. When used properly, fixatives may reduce the probability of colonization of the tissue by commonly occurring microorganisms (e.g., bacteria) that may be present in or around the tissue. In some cases, a fixation agent increases the mechanical strength or stability of the tissue, which may help to preserve the overall shape and structure of the sample as it is processed.

In some embodiments, the tissue sample may be stabilized by formalin fixation and paraffin embedding (i.e., an FFPE sample). Such stabilization makes the tissue permeable to staining reagents and amenable to cross-linking so that various macromolecules within the tissue become more stabilized. Fixation agents other than formalin may be used, such as glutaraldehyde or a freezing agent (e.g., liquid nitrogen).

The tissue sample may be stored for a suitable period of time. For example, if formalin fixed and paraffin embedded, the sample may be stored for relatively long periods of time (e.g., weeks, months, years) without suffering degradation or damage.

When the sample is embedded in paraffin, the overall temperature of the sample during processing may remain below a melting temperature of the paraffin. As a result, in some embodiments, paraffin may be disassociated from tissue sample material without causing bulk melting of the paraffin. Also, if the paraffin embedded sample is surrounded by an aqueous solution (non-solvent liquid), the sample may be rehydrated during paraffin disassociation. For example, exposing the sample to focused acoustic energy during a paraffin disassociation process may result in an opalescent-appearing liquid as the paraffin is emulsified or otherwise separated from tissue portions of the sample.

As discussed, the tissue sample may have any appropriate thickness. In some embodiments, the thickness of the tissue sample is less than about 100 microns, less than about 50 microns, less than about 30 microns, less than about 10 microns, less than about 5 microns, or less than about 1 micron. For example, the thickness of the tissue sample may be between about 0.1 micron and about 30 microns, between about 0.5 microns and about 10 microns, between about 5 microns and about 10 microns (e.g., approximately 7 microns thick), between about 1 micron and about 5 microns, or may be any other suitable thickness. In some embodiments, the tissue sample is microtome sectioned to a suitable thickness.

In some embodiments, the focused acoustic energy may have characteristics such that upon exposure of the sample to the acoustic energy, cavitation of the sample or material around the sample is minimal or, in some cases, does not occur at all. For example, acoustic energy having a relatively high acoustic frequency, in some instances, may result in a greater degree of attenuation in the system and, in many instances, may reduce the effects of cavitation. When little to no cavitation of or around the sample occurs, the probability that the sample, particularly for relatively thin tissue samples used for histology (e.g., less than 100 microns, less than 50 microns), becomes damaged during transfer between substrates is greatly reduced. Accordingly, it may be preferable to generate a level of focused acoustic energy that is sufficient so as to result in sample transfer between substrates, yet tempered such that little to no cavitation that would otherwise detrimentally affect sample analysis (e.g., histology) occurs.

The ability to retain histological quality of the transferred portion of the sample (e.g., immunohistochemically stained) may allow for various types of analyses and diagnoses to be performed. For instance, a sample may be analyzed so as to obtain a diagnosis as to whether the tissue is normal or malignant. Alternatively, or in addition, the tissue sample may be subject to any suitable molecular analyses (e.g., sequencing, biomarkers, etc.).

In some embodiments, the sample holder and/or initial substrate includes a material that generates energy when subject to acoustic energy, such as an inert energy transfer coating. For example, the tissue sample may be mounted on top of a suitable energy transfer coating. Focused acoustic energy applied to the coating material initiates the generation of kinetic energy, vaporizing the coating material and propelling the selected portion of the tissue sample from the initial substrate to the transfer substrate.

A number of exemplary processes for transferring a sample from one substrate to another according to various embodiments are now presented.

Figure 4:
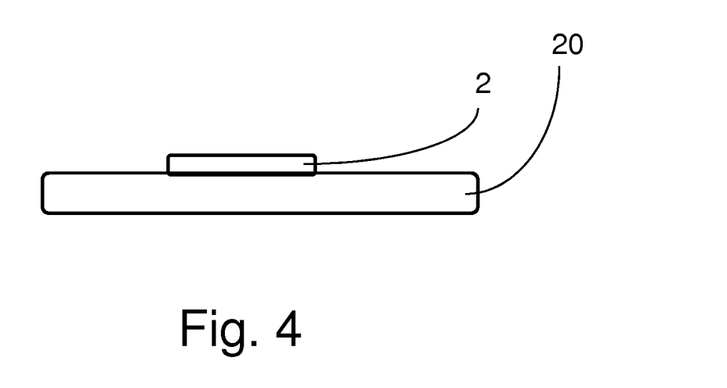
FIG. 4 shows a tissue sample and a substrate in accordance with some embodiments.

As shown in FIG. 4, a tissue sample (hard or soft tissue) is collected, such as via a biopsy or other method of collection. The tissue sample—which may or may not be fixed—may be appropriately sectioned and mounted on to a substrate. FIG. 4 depicts a tissue sample 2 placed on an initial substrate 20 (substrate holder not shown in the figures), such as a glass slide, which is adapted to be imaged using a microscope system.

Figure 5:
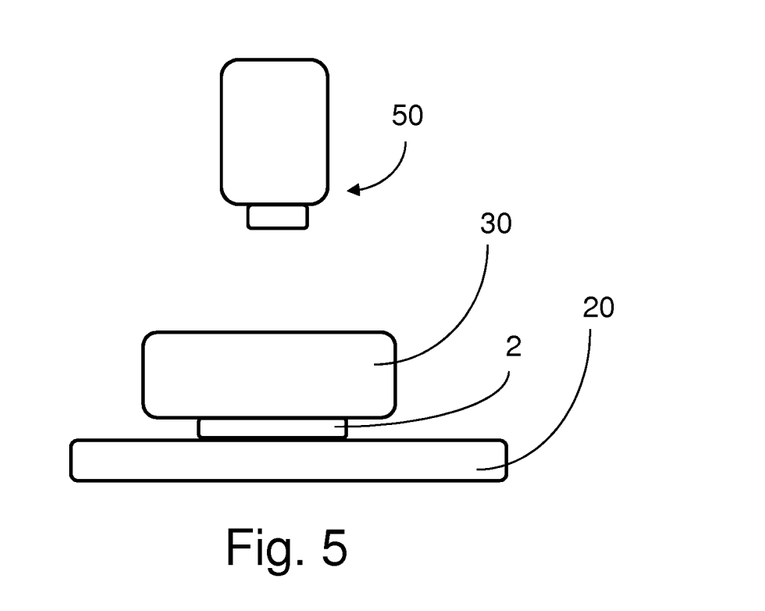
FIG. 5 illustrates a tissue sample disposed between a substrate and a transfer surface in accordance with some embodiments.

FIG. 5 illustrates the tissue sample 2 and initial substrate 20 positioned under a microscope apparatus 50. Similar to that shown in FIG. 2, a transfer substrate 30 is appropriately positioned adjacent to the tissue sample 2 and the initial substrate 20. In this embodiment, the transfer substrate 30 is transparent so that the tissue sample may be imaged through the transfer substrate.

Figure 6:
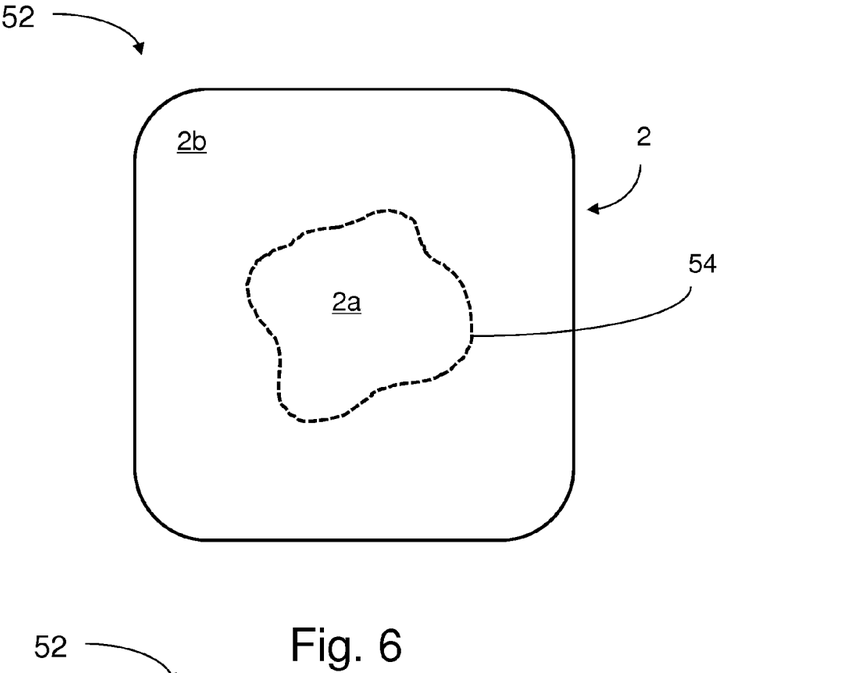
FIG. 6 shows a field of view of a sample in accordance with some embodiments.
Figure 7:
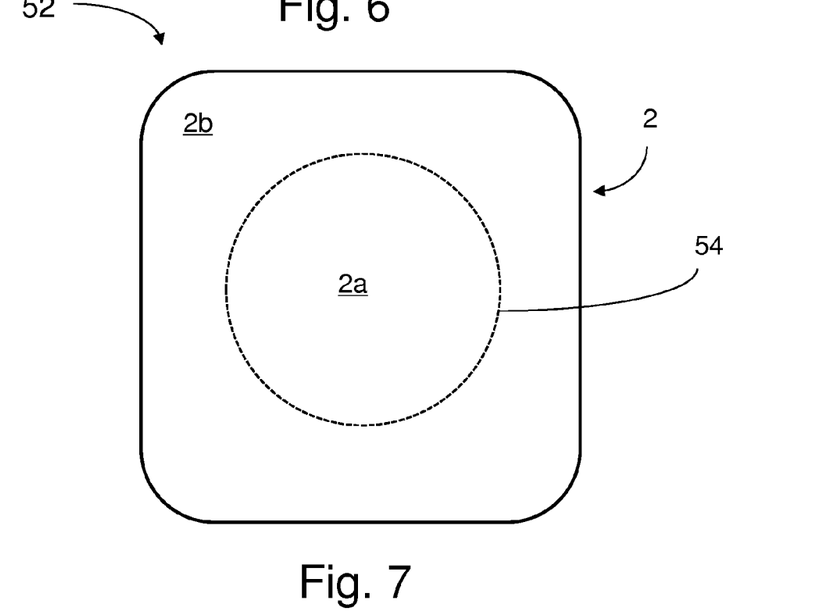
FIG. 7 illustrates another field of view of a sample in accordance with some embodiments.

FIGS. 6 and 7 depict various embodiments of a field of view 52 of the microscope, showing a region of the sample 2 that is positioned under the lens of the microscope. As discussed herein, the treatment system may be equipped with a control circuit that correlates the field of view of the microscope which is in optical focus with the location at which the focused acoustic energy may be applied. Or, in other words, the location of a focal zone of acoustic energy may be controlled based on an image produced by the microscope, the image either currently being visualized and/or stored in memory.

A user (or automated system) may select a region 2a of the sample to be transferred from the initial substrate 20 to a surface of the transfer substrate 30. Selection may be performed by any suitable method. For example, the field of view of the microscope may be displayed on a monitor and a user may operate a computer to manipulate a pointer (e.g., cursor) displayed on the monitor so as to trace out a boundary that surrounds the region of the sample where transfer from the initial substrate to the transfer substrate is desired. In some cases, focused acoustic energy having appropriate characteristics may be applied immediately once the selected portion of the sample is determined. Or, aspects of the selected region may be stored in memory for the focused acoustic energy to be applied at a later time.

FIG. 6 illustrates a selected region 2a (shown by the dotted line) that is enclosed by a traced-out boundary 54 which is effective to choose the portion of the sample to which focused acoustic energy is to be applied. A selected region 2a may have any suitable shape or size. For instance, FIG. 7 depicts a selected region 2a (shown by the dotted line) that has a boundary which happens to be circular in shape. Such selected regions may be manually or automatically determined by operation of the microscope in cooperation with the acoustic treatment system.

Figure 8:
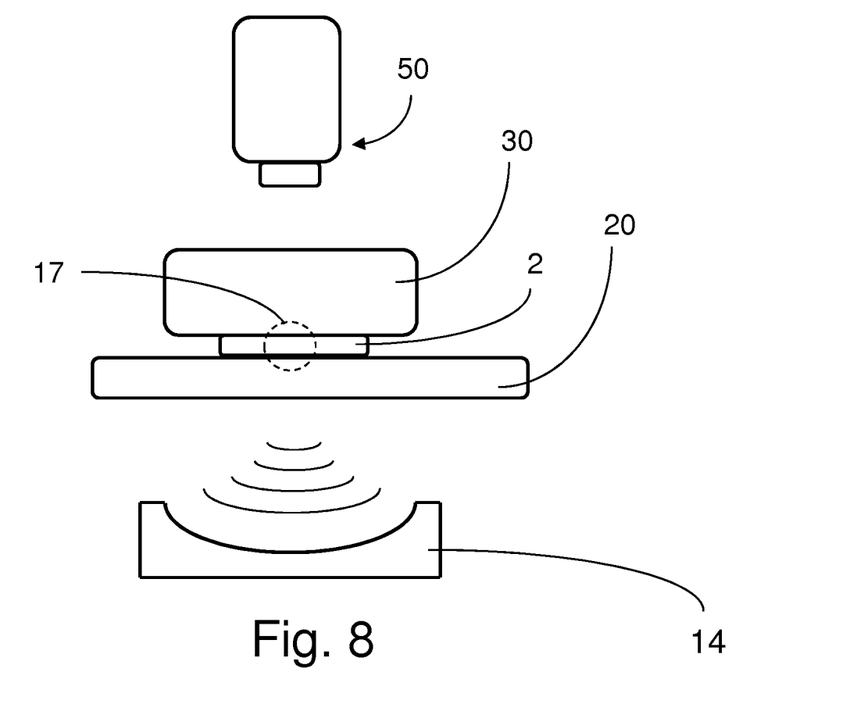
FIG. 8 depicts a tissue sample exposed to acoustic energy in accordance with some embodiments.

As discussed herein, focused acoustic energy is applied to the selected portion of the sample that is desired to be transferred. As shown in FIG. 8, and similar to that depicted in FIG. 2 (except without illustrating the coupling medium and control circuit), acoustic energy emitted from the transducer 14 converges to a focal zone 17 at the sample. In particular, the location of the focal zone of acoustic energy coincides with the selected region of the tissue sample 2.

Figure 9:
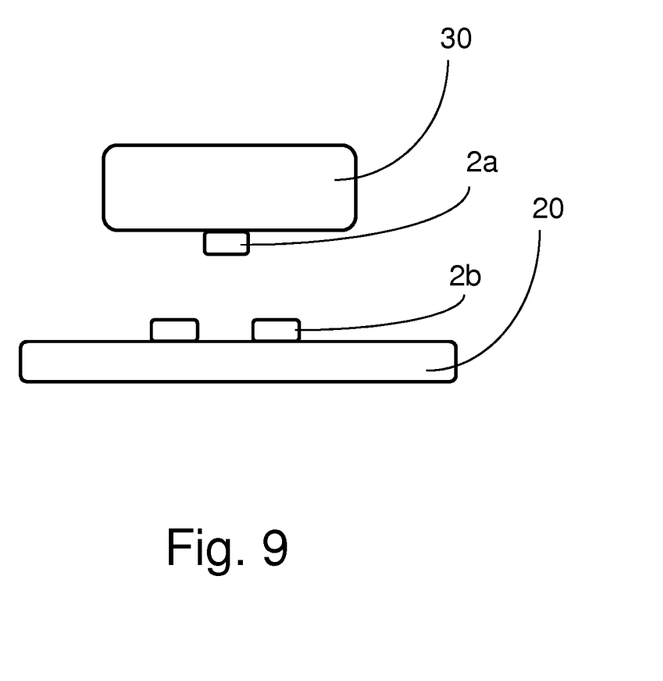
FIG. 9 shows a portion of a sample transferred from a substrate to a transfer surface in accordance with some embodiments.

FIG. 9 depicts transfer of the selected region 2a of the sample to the surface of the transfer substrate 30, while leaving an unselected region 2b of the sample to remain on the initial substrate 20. After transfer of the selected portion of the sample is completed, the transferred tissue may be appropriately analyzed (e.g., morphological study, histological study, imaging/microscopy, mass spectrometry, nucleic acid sequencing, etc.), or otherwise processed. In some embodiments, substantial portions of a sample (e.g., scroll sample) may be transferred in succession to appropriate substrates according to different subsequent purposes.

The resolution of the selected region(s) of the sample to be transferred may depend, in part, on the size of the focal zone of acoustic energy. For instance, a small focal zone of acoustic energy (e.g., width of less than 1 mm) may allow for a relatively small selected region of tissue sample to be transferred, or a selected region having a fine resolution.

Figure 10:
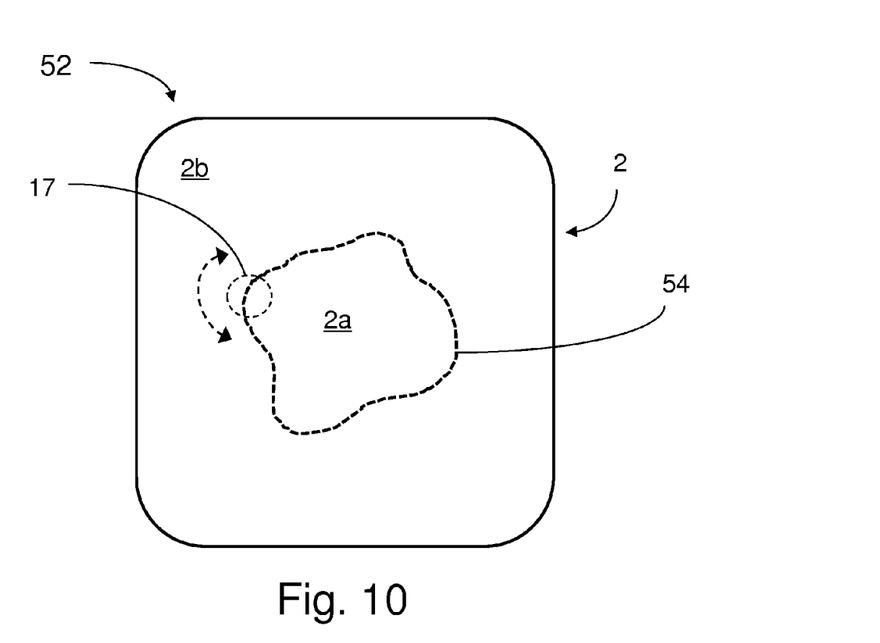
FIG. 10 shows a sample exposed to acoustic energy in accordance with some embodiments.
Figure 11:
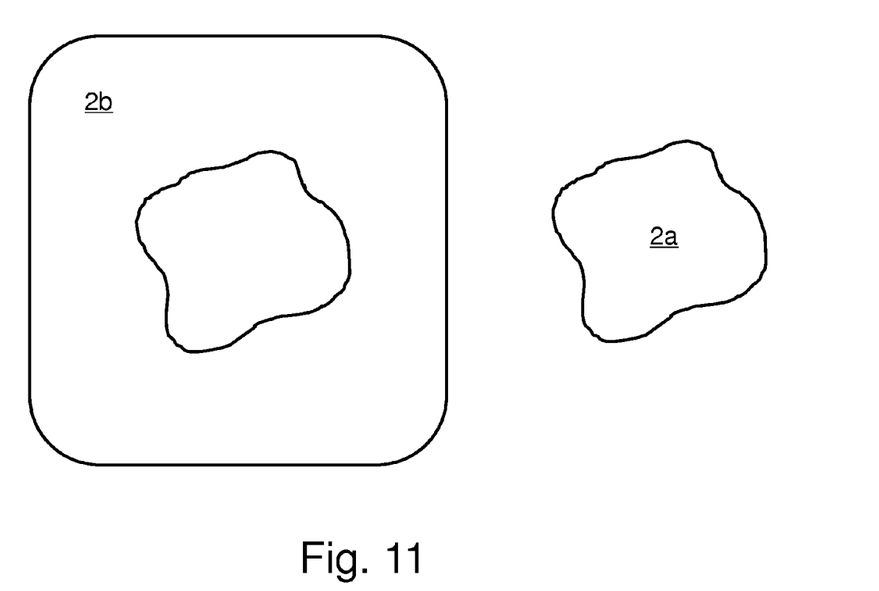
FIG. 11 depicts portions of the sample of FIG. 10 after exposure to the acoustic energy.

As shown in FIG. 10, the focal zone 17 of acoustic energy (shown by the dashed line) is small enough to trace out the boundary 54 of the selected region 2a of the sample (shown by the dotted line). As the focal zone 17 moves along the boundary 54, the selected region 2a of the sample is separated, or "cut out," from the initial substrate 20 and allowed to be removed from the unselected region 2b, which remains on the initial substrate. Accordingly, the selected region 2a of the sample may subsequently be transferred to the transfer substrate. FIG. 11 shows selected region 2a of the sample removed from the unselected region 2b (initial substrate and transfer substrate are not shown). Here, the edge of the removed selected region 2a corresponds to the boundary 54 originally traced out during selection of the portion to be transferred.

Figure 12:
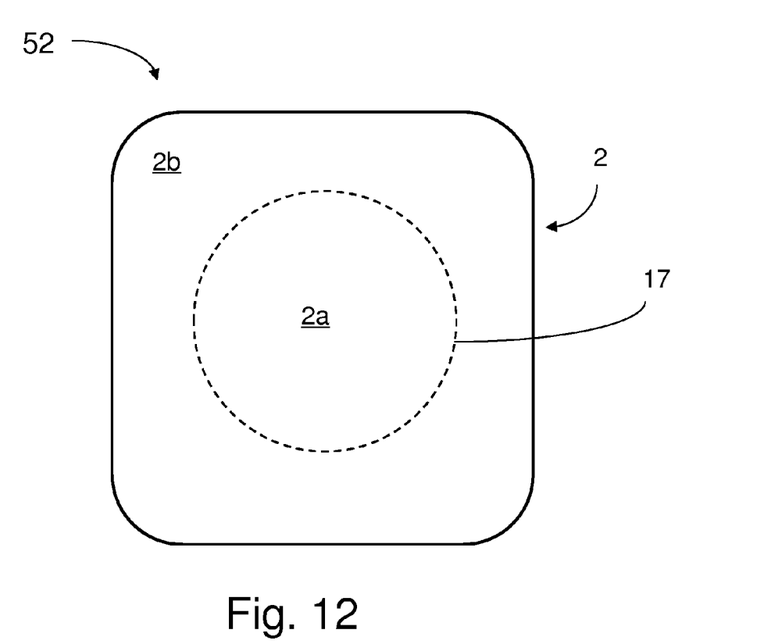
FIG. 12 shows another sample exposed to acoustic energy in accordance with some embodiments.
Figure 13:
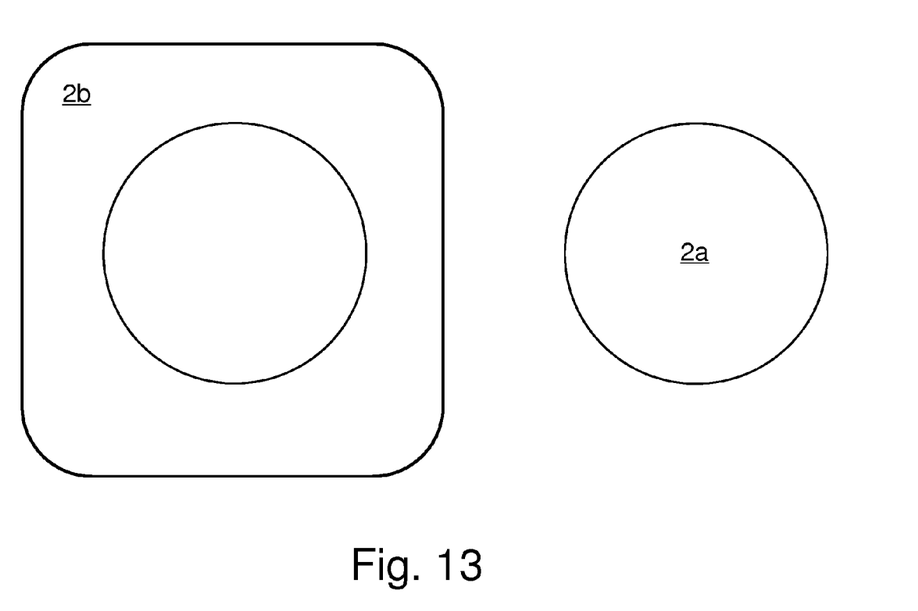
FIG. 13 depicts portions of the sample of FIG. 12 after exposure to the acoustic energy.

Alternatively, a relatively large focal zone of acoustic energy may cover the entire selected region 2a, causing the selected region 2a to separate from the initial substrate 20 and to be moved away from the region 2b that remains unselected. As shown in FIG. 12, the focal zone 17 of acoustic energy (shown by the dashed line) is large enough to cover the entire selected region 2a of the sample. After a suitable level of exposure, the selected region 2a of the sample is separated from the initial substrate 20 so as to be transferred to the transfer substrate 30. FIG. 13 depicts selected region 2a of the sample removed from the unselected region 2b. As discussed above, in some embodiments, a line-shaped focal zone may be applied as a scan over a substantial area of a sample for more rapidly transferring that scanned area from one substrate to another.

As described above, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the sample holder, initial substrate or other components, position sensors to indicate positions of the acoustic transducer 14 and/or the sample holder or initial substrate, and so on), user data input devices (such as buttons, dials, knobs, a keyboard, a touch screen or other), information display devices (such as an LCD display, indicator lights, a printer, etc.), and/or other components for providing desired input/output and control functions.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

What is claimed is:

1. A method of processing a sample, comprising:
providing a substrate supporting a tissue sample;
imaging a portion of the tissue sample;
defining a boundary of a region of the tissue sample to be transferred from the substrate on an image of the portion of the tissue sample;
positioning a transfer surface adjacent to the substrate such that the sample is disposed between the substrate and the transfer surface; and
transferring the entire region of the tissue sample from the substrate to the transfer surface such that the transfer surface supports the region of the tissue sample by exposing the region of the tissue sample to focused acoustic energy having a frequency of about 100 kHz to 100 MHz generated from an acoustic energy source, the entire region of the tissue sample being transferred to the transfer surface while other parts of the tissue sample remain on the substrate.

2. The method of claim 1, wherein imaging the portion of the tissue sample to be transferred comprises imaging a portion of the tissue sample that is to be located within a focal zone of the acoustic energy.

3. The method of claim 1, wherein the step of defining a boundary includes tracing the boundary on the image using a pointer.

4. The method of claim 3, wherein transferring the entire region of the tissue sample from the substrate to the transfer surface comprises exposing the entire region of the tissue sample to a focal zone of the acoustic energy.

5. The method of claim 3, wherein transferring the entire region of the tissue sample from the substrate to the transfer surface comprises scanning a focal zone of the acoustic energy across the region of the tissue sample.

6. The method of claim 1, wherein transfer of the entire region of the sample from the substrate to the transfer surface occurs at a temperature below 60 degrees C.

7. The method of claim 1, wherein exposing the region of the tissue sample to focused acoustic energy comprises generating acoustic energy having a frequency of between about 0.1 MHz and about 3 MHz and a focal zone of acoustic energy having a width of less than about 1 cm.

8. The method of claim 1, wherein the step of transferring includes transmitting the acoustic energy from the acoustic energy source through the substrate toward the tissue sample.

9. The method of claim 1, wherein the step of transferring includes transmitting the acoustic energy from the acoustic energy source through the transfer surface toward the tissue sample.

10. The method of claim 1, wherein exposing the region of the tissue sample to focused acoustic energy comprises causing vibration of the portion of the tissue sample.

11. The method of claim 1, wherein exposing the region of the tissue sample to focused acoustic energy comprises causing an impedance mismatch at an interface between the substrate and the region of the tissue sample to be transferred.

12. The method of claim 1, wherein transferring of the entire region of the tissue sample from the substrate to the transfer surface occurs without cavitation.

13. The method of claim 1, wherein transferring of the entire region of the tissue sample occurs in a substantially dry environment.

14. The method of claim 1, wherein transferring of the entire region of the tissue sample occurs in a substantially wet environment.

15. The method of claim 1, further comprising:
   tracing a boundary of the region of the tissue sample by a focal zone of the acoustic energy to separate the region from a remaining portion of the tissue sample.

* * * * *